US011571590B2

(12) United States Patent
Wang

(10) Patent No.: US 11,571,590 B2
(45) Date of Patent: *Feb. 7, 2023

(54) RADIATION METHOD AND APPARATUS FOR RADIATING A FLUENCE MAP HAVING ZERO FLUENCE REGION

(71) Applicant: SHANGHAI UNITED IMAGING HEALTHCARE CO., LTD., Shanghai (CN)

(72) Inventor: Weiyuan Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 101 days.

This patent is subject to a terminal disclaimer.

(21) Appl. No.: 17/139,095

(22) Filed: Dec. 31, 2020

(65) Prior Publication Data

US 2021/0121714 A1    Apr. 29, 2021

Related U.S. Application Data

(63) Continuation of application No. 16/433,737, filed on Jun. 6, 2019, now Pat. No. 10,881,876, which is a (Continued)

(30) Foreign Application Priority Data

Dec. 30, 2015 (CN) .......................... 201511024949.6

(51) Int. Cl.
A61N 5/10 (2006.01)
(52) U.S. Cl.
CPC .......... *A61N 5/1036* (2013.01); *A61N 5/1045* (2013.01)

(58) Field of Classification Search
CPC ...... A61N 5/1036; A61N 5/1045; A61N 5/00; A61N 5/1031
See application file for complete search history.

(56) References Cited

U.S. PATENT DOCUMENTS 6,266,393 B1    7/2001  Ein-Gal
10,315,048 B2 * 6/2019  Wang ................... A61N 5/1036
(Continued)

FOREIGN PATENT DOCUMENTS

CN           2605027 Y     3/2004
CN         101120871 A     2/2008
(Continued)

*Primary Examiner* — Courtney D Thomas
(74) *Attorney, Agent, or Firm* — Metis IP LLC

(57) ABSTRACT

The present disclosure provides a radiation method for radiating a fluence map having a zero-fluence region under a movement of MLC (Multi-Leaf Collimator) includes a determining step of determining at least one basic fluence map from the fluence map. The basic fluence map includes a first non-zero fluence region and a second non-fluence region having the zero-fluence region therebetween. The radiation method includes a first radiating step including radiating the first non-zero fluence region, along with moving a first group of leaf pairs and moving a vertical jaw to shade the first group of leaf pairs, and a second radiating step including radiating the second non-zero fluence region, along with moving a second group of leaf pairs and withdrawing the vertical jaw to expose the second group of leaf pairs.

20 Claims, 14 Drawing Sheets

Related U.S. Application Data continuation of application No. 15/394,829, filed on Dec. 30, 2016, now Pat. No. 10,315,048.

(56) References Cited

U.S. PATENT DOCUMENTS

| | | | |
|---|---|---|---|
| 10,881,876 B2* | 1/2021 | Wang | ................... A61N 5/1036 |
| 2004/0190680 A1 | 9/2004 | Chang | |

FOREIGN PATENT DOCUMENTS

| | | |
|---|---|---|
| CN | 104835547 A | 8/2015 |
| WO | 2014013013 A1 | 1/2014 |

* cited by examiner

RADIATION METHOD AND APPARATUS FOR RADIATING A FLUENCE MAP HAVING ZERO FLUENCE REGION

CROSS-REFERENCE TO RELATED APPLICATIONS

This application is a continuation of U.S. application Ser. No. 16/433,737, filed Jun. 6, 2019, which is a continuation of U.S. application Ser. No. 15/394,829, filed on Dec. 30, 2016 now U.S. Pat. No. 10,315,048, which in turn claims priority of Chinese Patent Application No. 201511024949.6 filed Dec. 30, 2015, the contents of each of which are hereby incorporated by reference.

TECHNICAL FIELD

The present disclosure generally relates to radiation method and an apparatus used in radiation therapy, and more particularly, a radiation method for a fluence map having zero fluence region and an apparatus thereof.

BACKGROUND

Along with the development of medical theories such as the radiophysics, radiobiology, clinical oncology etc., together along with the development of medical imaging apparatus and computer technology, radiotherapy (hereinafter referred as RT) technology is continuously developed to satisfy clinic requirement better. Due to a great development from conventional RT technology to 3D conformal radiation therapy (3DCRT), RT technology becomes more precise. Therefore, both a partial recurrence rate of tumor and an occurrence rate of normal tissue complication are greatly reduced. Intensity-modulated radiation therapy (IMRT), developed on 3DCRT, is able to conform radiation to the size, shape and location of a target region more precisely, to protect OAR (Organ At Risk) around the target region more effectively.

A basic principle of IMRT is dividing the radiation field (beam field) into multiple small segment fields (beamlets) with different intensities to thereby optimize radiation delivery. In this way, the intensity of a beamlet through OAR is reduced while the intensity of a beamlet through the target region is increased. Multi-leaf collimator (MLC) is introduced to radiate a fluence map in IMRT. Especially to a target region having a recess in which OAR is positioned, IMRT technology can be performed more effectively.

The fluence map used in IMRT is possibly shaped into a U-shape or an O-shape, to leave a recess for OAR. The fluence map is discretized with zero fluence region and non-zero fluence region, as shown in FIG. 1. It is called subsectional fluence distribution.

According to conventional field dividing radiation method, in order to radiate the radiation field having subsectional fluence distribution, the radiation field is divided into two or more segment fields. Firstly, one segment field is radiated.

Subsequently, jaws and MLC are moved to the next segment field when radiation is closed. Jaws comprises parallel Jaws moving along a direction parallel to a moving direction of the MLC, and perpendicular jaws moving along a direction perpendicular to the moving direction of the MLC.

FIGS. 15(a)-15(f) are schematic figures showing a process of radiating a U-shaped fluence map with the conventional field-dividing method. Firstly, the left half of the fluence map is radiated. When the left half of the fluence map has finished to be radiated, the jaws and the MLC are moved to the right half of the fluence map. In the process of moving the jaws and MLC, the radiation is closed and the fluence map is not radiated. When the jaws and MLC have been moved to the right half of the fluence map, the right half of the fluence map begins to be radiated.

However, the field-dividing method may have some defects. In the method, a beam field may be divided into a plurality of segment fields. Radiation of the plurality of segment fields may increase total MU. For example, the total MU (Monitor Unit) may increase approximately one time to the original minimum total MU once one beam field is added. Besides, if radiation of a segment field is completed, the jaws and the MLC may move to next segment field. The moving of the jaws and the MLC may take time. The time spent on the moving may be referred as a 'set-up time'. The total treatment time may be increased accordingly. Further, there may be penumbra at the edge of segment field. Thus, doses delivered at the edge of adjacent segment fields may be inaccurate.

SUMMARY

The objective of present invention is to provide a radiation method and apparatus for radiating a fluence map having zero-fluence regions once for reducing MU and save the time of treatment.

In one embodiment of the present invention, a radiation method for radiating a fluence map having a zero-fluence region under a movement of MLC includes a determining step of determining a basic fluence map from the fluence map. The basic fluence map comprises at least one region group each having a first non-zero fluence region and a second non-fluence region have the zero fluence region positioned therebetween. The radiation method further includes a first radiating step including radiating the first non-zero fluence region, along with moving a first group of leaf pairs of the MLC in the first non-zero fluence region and moving a vertical jaw to shade the first group of leaf pairs. The radiation method further includes a second radiating step including radiating the second non-zero fluence region, along with moving a second group of leaf pairs of the MLC in the second non-zero fluence region and withdrawing the vertical to expose the second group of leaf pairs.

In one embodiment of the present invention, in the first radiating step, the vertical jaw is moved along a vertical direction perpendicular to the moving direction of the first group of leaf pairs to shade part of the first group of leaf pairs which have finished to play a part in radiating the first non-zero fluence region in sequence.

In one embodiment of the present invention, in the first radiating step, the vertical jaw is moved along a vertical direction perpendicular to the moving direction of the first group of leaf pairs to shade part of the first group of leaf pairs which have finished to play a part in radiating the first non-zero fluence region in sequence.

In one embodiment of the present invention, in the second radiating step, the vertical jaw is withdrawn along the vertical direction to expose the second group of leaf pairs which begin to play a part in radiating the second non-zero fluence region in sequence.

In one embodiment of the present invention, the first group of leaf pairs and the second group of leaf pairs are at least partly same.

In one embodiment of the present invention, the basic fluence map further comprises a third non-fluence region communicating with the first non-zero fluence region and the second non-zero fluence region. The first radiating step further includes radiating a first part of the third non-zero fluence region along with moving a third group of leaf pairs of the MLC in the third non-zero fluence region. The second radiating step further includes radiating a second part of the third non-zero fluence region along with moving the third group of leaf pairs in the third non-zero fluence region.

In one embodiment of the present invention, said basic fluence map is of a substantially U-shape and comprises one said region group.

In one embodiment of the present invention, a vertical dimension of the first non-zero fluence region is identical to that of second non-zero fluence region, and the number of the first group of leaf pairs is identical to that of the second group of leaf pairs.

In one embodiment of the present invention, a vertical dimension of the first non-zero fluence region is greater than that of second non-zero fluence region, and the number of the first group of leaf pairs is greater than that of the second group of leaf pairs.

In one embodiment of the present invention, a vertical dimension of the first non-zero fluence region is smaller than that of second non-zero fluence region, and the number of the first group of leaf pairs is less than that of the second group of leaf pairs.

In one embodiment of the present invention, the basic fluence map is of a X-shape and comprises two region groups. The first radiating step includes radiating the first non-zero fluence region of each region group along with moving the vertical jaw. The second radiating step includes radiating the second non-zero fluence region of each region group along with the moving the vertical jaw.

In one embodiment of the present invention, the radiation method further comprises a further radiating step of radiating a middle part between the first part and the second part of the third non-zero fluence region happened between the first radiating step and the second radiating step.

In one embodiment of the present invention, the radiation method further comprises a moving step of moving the first group of leaf pairs into an initial position of the first non-zero fluence region before the first radiating step.

In one embodiment of the present invention, a radiation method for radiating a fluence map having a zero-fluence region under a movement of MLC includes a dividing step of dividing the fluence map into a number basic fluence maps. The basic fluence map comprises at least one region group each having a first non-zero fluence region and a second non-fluence region having the zero-fluence region positioned therebetween. The radiation method further includes a radiating step of radiating each basic fluence map. The radiating step includes a first radiating step including radiating the first non-zero fluence region, along with moving a first group of leaf pairs of the MLC in the first non-zero fluence region and moving a vertical jaw along a vertical direction perpendicular to the moving direction of the first group of leaf pairs to shade the first group of leaf pairs. The radiation method further includes a second radiating step including radiating the second non-zero fluence region, along with moving a second group of leaf pairs of the MLC in the second non-zero fluence region and withdrawing the vertical jaw along the vertical direction to expose the second group of leaf pairs.

In radiating each basic fluence map, the first and second groups of leaf pairs are moved along an invariable direction and the basic fluence map is radiated once.

In radiating the plurality of basic fluence maps, the first and second groups of leaf pairs are moved repeatedly in radiating different basic fluence maps.

In one embodiment of the present invention, the first group of leaf pairs and the second group of leaf pairs are at least partly same. In the first radiating step, the vertical jaw is moved along a vertical direction perpendicular to the moving direction of the first group of leaf pairs to shade part of the first group of leaf pairs which have finished to play a part in radiating the first non-zero fluence region in sequence. In the second radiating step, the vertical jaw is withdrawn along the vertical direction to expose part of the second group of leaf pairs which begin to play a part in radiating the second non-zero fluence region in sequence.

In one embodiment of the present invention, the basic fluence map further comprises a third non-fluence region communicating with the first non-zero fluence region and the second non-zero fluence region. The first radiating step further includes radiating a first part of the third non-zero fluence region along with moving a third group of leaf pairs of the MLC in the third non-zero fluence region. The second radiating step further includes radiating a second part of the third non-zero fluence region along with moving the third group of leaf pairs in the third non-zero fluence region.

In one embodiment of the present invention, the basic fluence map is of a substantially U-shape and comprises one region group.

In one embodiment of the present invention, the basic fluence map is of a substantially X-shape and comprises two said region groups. The first radiating step includes radiating the first non-zero fluence region of each region group along with moving the vertical jaw. The second radiating step includes radiating the second non-zero fluence region of each region group along with the moving the vertical jaw.

In one embodiment of the present invention, a radiating apparatus applied in radiating a fluence map having a zero-fluence region under a movement of MLC includes a determining module and a driving module. The determining module is used to determine at least one basic fluence map from the fluence map. The basic fluence map is adapted for being radiated once along an invariable direction and comprises a first non-zero fluence region and a second non-fluence region having the zero-fluence region positioned therebetween. The driving module is used to drive a first group of leaf pairs of the MLC to move in the first non-zero fluence region, moving the vertical jaw along a direction perpendicular to the moving direction of the first group of leaf pairs to shade the first group of leaf pairs, driving a second group of leaf pairs of the MLC move in the second non-zero fluence region, and withdrawing the vertical jaw to expose the second group of leaf.

As compared with prior art, the fluence map in the present invention can be radiated once, rather than be radiated several times. MU is correspondingly reduced. In addition, it will be more efficiently to radiate the fluence map of the present invention, since the "set-up time" is saved. The treatment time may be reduced accordingly. Furthermore, the fluence map is radiated once, dose delivered at the edge of adjacent fluence region is accurate.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
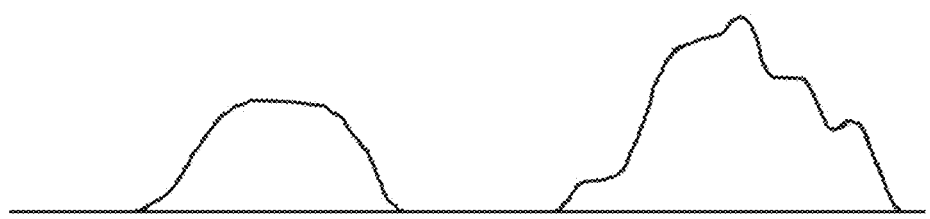
FIG. 1 is a schematic figure of 1-D of a fluence map having a zero fluence region.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

In order to clearly understand the objective, features, and advantages of the present invention, the embodiments of the present invention are described in combination with the companying drawings as follows.

In the following description, more details are described for understanding the present invention fully, but other embodiments different from the recitation here also can be used by the present invention. Therefore, the present invention is not limited by the specific embodiments disclosed hereinafter.

The embodiment of the present invention recites a radiation method radiating a fluence map having zero fluence region and the apparatus used in the radiation method, which is adapted for being applied in IMRT. It is possible to radiate a fluence map having zero fluence region once.

Figure 2A:
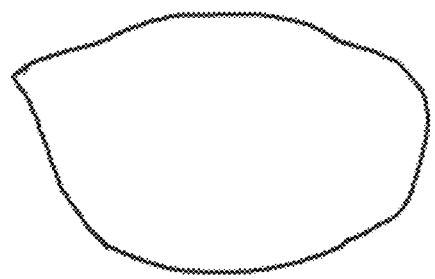
FIG. 2(a) is a schematic figure showing a convex-shaped fluence map.
Figure 2B:
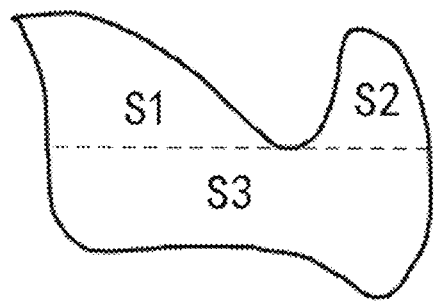
FIG. 2(b) is a schematic figure showing a substantially U-shaped fluence map.
Figure 2C:
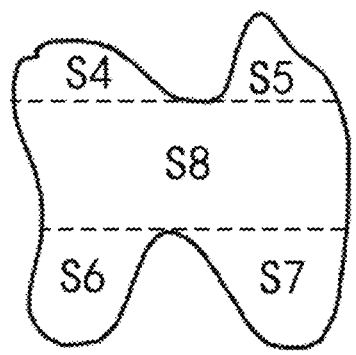
FIG. 2(c) is a schematic figure showing a substantially X-shaped fluence map.

FIGS. 2(a)-2(c) show three types of basic shapes of the fluence map. FIG. 2(a) shows a convex-shaped fluence map having a convex-shaped contour without any recess. No subsectional fluence distribution is formed in the convex-shaped fluence map. In conjunction with FIG. 3, the convex-shaped fluence map can be radiated under the movement of the MLC 310 only, without a participation of the vertical jaw.

FIG. 2(b) shows a substantially U-shaped fluence map having a first recess opened upwardly. Optionally, the first recess can be opened downwardly. The first recess has a zero fluence region formed therein. Subsectional fluence distribution is formed along a moving direction of the MLC 310. It is impossible to radiate the substantially U-shaped fluence map under the movement of the MLC 310 directly due to the subsectional fluence distribution. The substantially U-shaped fluence map can be divided into a non-zero fluence region S1 in front of the first recess, a non-zero fluence region S2 behind the first recess, and a non-zero fluence region S3 below the first recess. A zero fluence region is positioned between the non-zero fluence region S1 and the non-zero fluence region S2 along the moving direction of the MLC 310, or along a direction substantially parallel to the moving direction of the MLC 310. The non-zero fluence region S3 communicates with the non-zero fluence region S1 and the non-zero fluence region S2 along a direction perpendicular to the moving direction of the MLC 310. The substantially U-shaped fluence map, as shown in FIG. 2(b), needs to be radiated under the cooperation of the MLC 310 and one perpendicular jaw 320 moving along a direction perpendicular to the moving direction of the MLC 310.

FIG. 2(c) shows a substantially X-shaped fluence map having an upper recess opened upwardly and a lower recess opened downwardly. The upper recess and the lower recess respectively have a zero fluence region formed therein.

Subsectional fluence distribution is formed along the moving direction of the MLC 310, or along a direction parallel to the moving direction of the MLC 310. It is impossible to radiate the substantially U-shaped fluence map under the movement of the MLC 310 directly due to the subsectional fluence distribution. The substantially X-shaped fluence map can be divided into a non-zero fluence region S4 in front of the upper recess, a non-zero fluence region S5 behind the upper recess, a non-zero fluence region S6 in front of the lower recess, a non-zero fluence region S7 behind the lower recess, and an eighth non-zero fluence region communicating with the non-zero fluence regions S4-S7. A zero fluence region is positioned between the non-zero fluence region S4 and the non-zero fluence region S5 along the moving direction of MLC 310, or along a direction substantially parallel to the moving direction of MLC 310. Another zero fluence region is positioned between the non-zero fluence region S6 and the non-zero fluence region S7 along the moving direction of MLC 310, or along a direction substantially parallel to the moving direction of MLC 310. The substantially X-shaped fluence map, as shown in FIG. 2(c), needs to be radiated under the cooperation of the MLC 310 and two perpendicular jaws 320 moving along a direction perpendicular to the moving direction of MLC 310.

Figure 3:
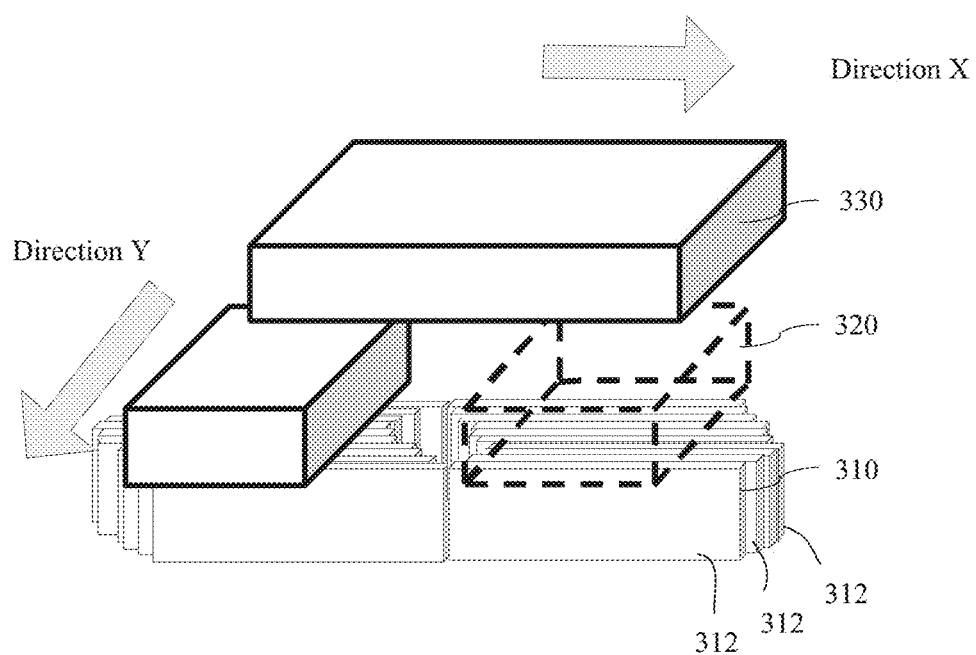
FIG. 3 is a schematic figure of jaws and MLC.

Referring to FIG. 3, MLC 310 comprises a plurality leaf pairs 312 movable along a direction X. Each pair of leaves 312 are movable along the direction X as marked in FIG. 3. Each leaf pair 312 can be opened and folded to control a size of an opening therebetween. When the leaf pair 312 is closed, there is a gap existed between the leaf pair 312 to avoid the leaves colliding each other. The parallel jaw 320 moves along the direction X parallel to a moving direction of the leaf pair 312. The perpendicular jaw 330 moves along the direction Y perpendicular to a moving direction of the leaf pair 312. The leaf pair 312 of the MLC 310 can be shaded by the parallel jaws 320 and the perpendicular jaws 330. In common radiotherapy apparatus, the parallel jaws 320 and perpendicular jaws 330 are used to confine the range of the radiation field, for example, to confine a rectangular range. Furthermore, in this range, a contour of the radiation field is defined by multiple leaf pairs of the MLC 310. In all of the embodiments of the present invention, contour of the radiation field is confined by multiple leaf pairs 312 of the MLC 310 together with the perpendicular jaws 330.

Figure 4:
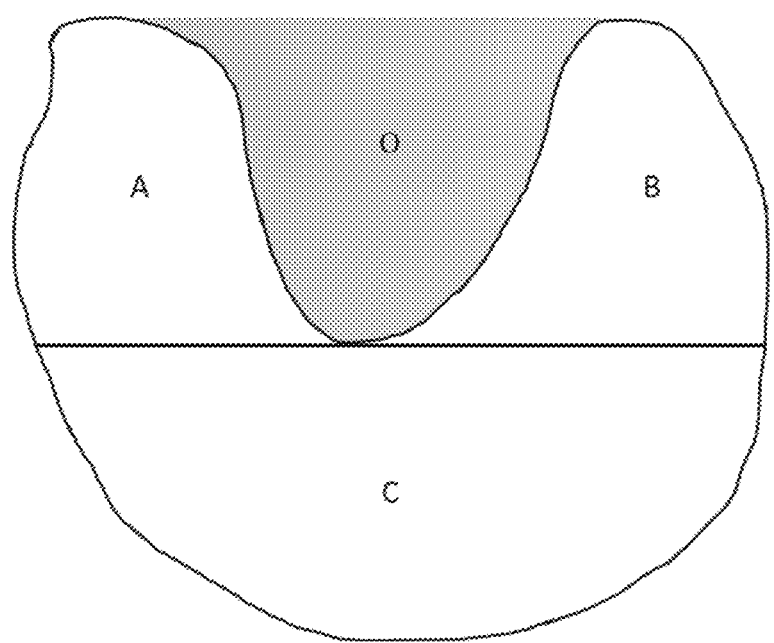
FIG. 4 is a schematic figure of the substantially U-shaped fluence map comprising a first through third non-zero fluence regions.

In a first embodiment, a process of radiating a substantially U-shaped fluence map shown in FIG. 4 is illustrated below. A substantially U-shaped fluence map can be divided into a non-zero fluence region A in front of a zero fluences region, a non-zero fluence region B behind the zero fluences region, and a non-zero fluence region C below the zero fluences region. The non-zero fluence region A is separated from the non-zero fluence region B by the zero fluence region along the moving direction of the MLC 310. The non-zero fluence region C communicates with the non-zero fluence region A and the non-zero fluence region B along a direction perpendicular to the moving direction of the MLC 310.

Figures 5A, 5B, 5C, 5D, 5E, 5F, 5G:
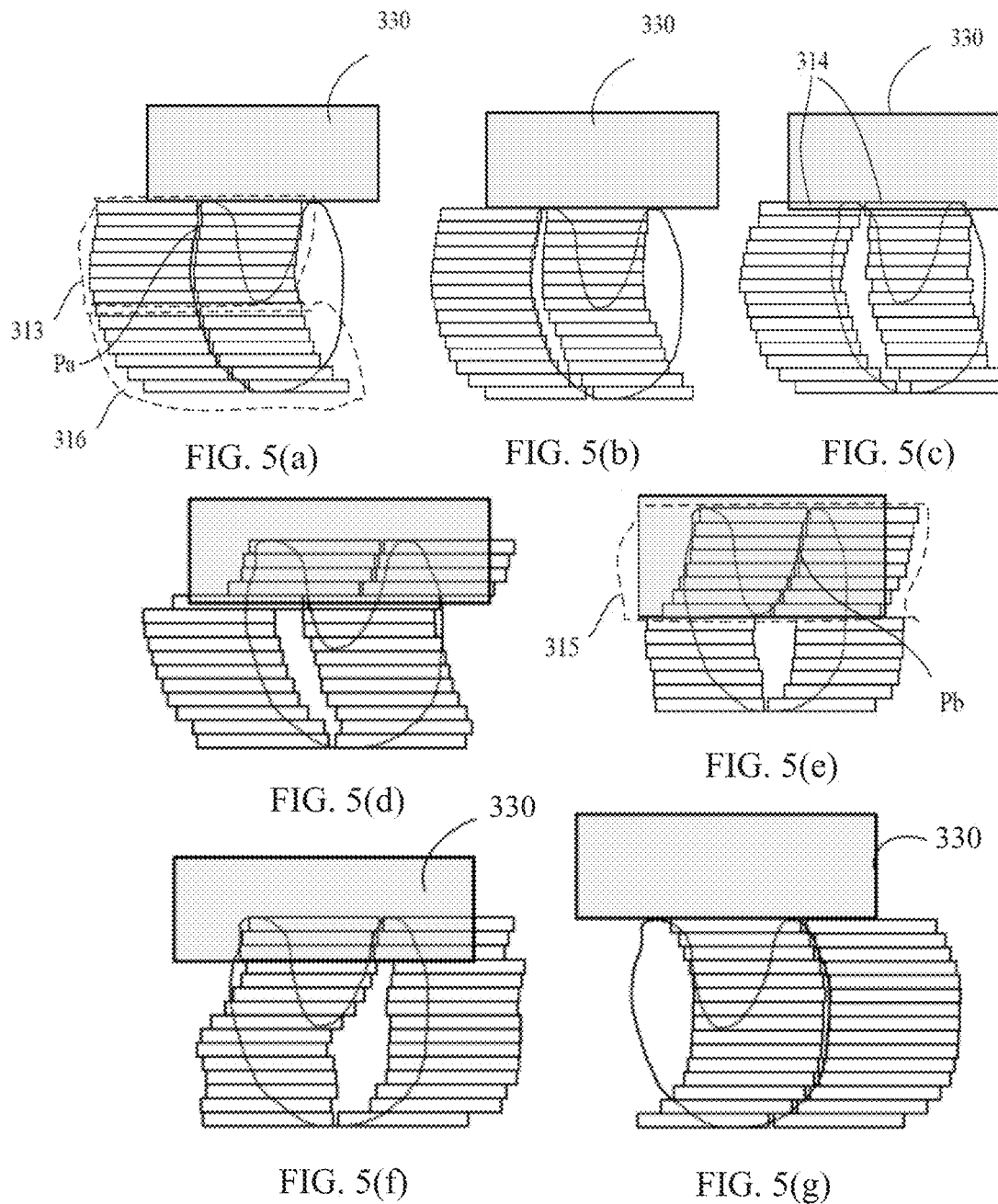
FIGS. 5(a)-5(g) are schematic figures showing a process of radiating the substantially U-shaped fluence map referred in a first embodiment of the present invention.
Figure 6:
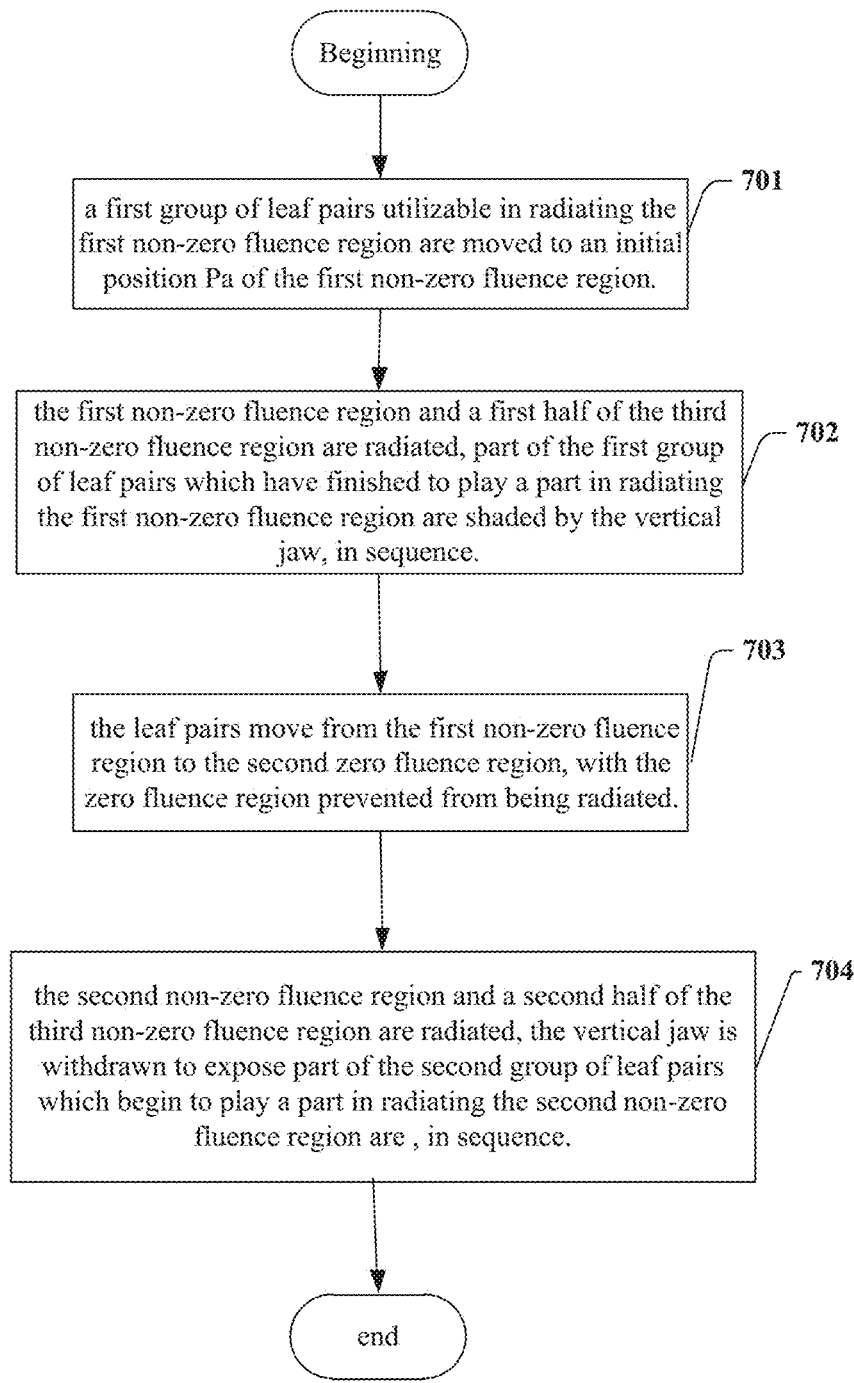
FIG. 6 is a flowchart showing the process of radiating the fluence map shown in FIGS. 5(a)-5(g) referred in the first embodiment of the present invention.

FIG. 6 is a flowchart showing a process of radiating the substantially U-shaped fluence map having the zero fluence region referred in the first embodiment. FIGS. 5(a)-5(g) are schematic figures showing a process of radiating the substantially U-shaped fluence map of the first embodiment. Referring to FIG. 5(a), in a step 701, a first group of leaf pairs 313 utilizable in radiating the first non-zero fluence region A are moved to an initial position Pa of the first non-zero fluence region A. A third group of leaf pairs 316 utilizable in radiating a left half of the third non-zero fluence region C are moved to a left edge of the third non-zero fluence region C.

In the step 702, the first non-zero fluence region A is radiated from left to right gradually through an upper part of the opening between the leaves of the leaf pairs 313 in the first group, along with the movement of the leaf pairs 313 and the downwardly movement of the vertical jaw 330. Meanwhile, the left half of the third non-zero fluence region C is radiated from left to right gradually through the lower part of the opening between the leaves of the leaf pairs 316 in the third group, along with the movement of the leaf pairs 316. In the process of radiating the first non-zero fluence region A and the left half of third non-zero fluence region C, part of the leaf pairs 313 which have already finished to play a part in radiating the first non-zero fluence region A are shaded by the vertical jaw 330 under the downwardly movement of the vertical jaw 330, in sequence.

Specifically, referring to FIG. 5(b), the leaf pairs 313, 316 move along a direction from left to right gradually. The first non-zero fluence region A and the left half of the third non-zero fluence region C are radiated through the opening between the leaves in the leaf pairs 313, 316. Referring to FIG. 5(c), the uppermost leaf pair 313a, which has already finished to play a part in radiating the uppermost part of the first non-zero fluence region A, is partially shaded by the vertical jaw 330, along with the downwardly movement of the vertical jaw 330. Referring to FIG. 5(d), upper leaf pairs of the leaf pairs 313, which have finished to play a part in radiating the upper portion of first non-zero fluence region A, are shaded by the vertical jaw 330, along with the further downwardly movement of the vertical jaw 330. The first non-zero fluence region A and the left half of the third non-zero fluence region C continue to be radiated through the opening between the leaves of the unshaded leaf pairs 313 in the first group and the leaf pairs 316 in the third group. Referring to FIG. 5(e), the vertical jaw 330 continues to move downwardly till arriving at a bottom of the first non-zero fluence region A. The first group of leaf pairs 313 are completely shaded by the vertical jaw 330 at that moment. The first non-zero fluence region A and a left half of the third non-zero fluence region C are radiated completely.

In the step 703, MLC continues to move along the direction from left to right, to carry a second group of the leaf pairs 315 to an initial position Pb of the second non-zero fluence region B. The zero fluence region is prevented from being radiated when the leaf pairs 315 move from the first non-zero fluence region A to the second non-zero fluence region B, since the zero fluence region is shaded by the vertical jaw 330 when the vertical jaw 330 arrives at the bottom of the first non-zero fluence region A, i.e., at a bottom of the zero fluence region. The leaf pairs 313 in the first group and the leaf pairs 315 in the second group are at least partly same.

In the step 704, the vertical jaw 330 is withdrawn upwardly to expose the leaf pairs 315 which begin to play a part in radiating the second non-zero fluence region B in sequence, when the second non-zero fluence region B and right half of the third non-zero fluence region C are radiated. Once the MLC 310 arrives at the bottom of the first non-zero fluence region A, the MLC 310 begins to leave from the bottom. The end of step 702 and the beginning of the step 704 happen almost the same time, with the MLC 310 and the vertical jaw 330 moving constantly.

Specifically, referring to FIGS. 5(e) and 5(f), the third non-zero fluence region C is radiated gradually through the lower part of the opening between the leaves in the leaf pairs 316 of the third group, along with the further rightward movement of the leaf pairs 316. Meanwhile, the second non-zero fluence region B begins to be radiated and then is radiated gradually through the upper part of the opening between the leaves in the leaf pairs 315 in the second group, along with the movement of the leaf pairs 315 and the upwardly movement of the vertical jaw 330. In the process of radiating the second non-zero fluence region B and the right half of the third non-zero fluence region C, the vertical jaw 330 is withdrawn to expose part of the leaf pairs 315 which begin to play a part in radiating the second non-zero fluence region B, in sequence.

Referring to FIG. 5(f), the second non-zero fluence region B and the right half of third non-zero fluence region C continue to be radiated through the opening between the leaves of the rest leaf pairs 315 of the second group and between the leaves of the leaf pairs 316 of the third group. Referring to FIG. 5(g), the second non-zero fluence region B and the third non-zero fluence region C are radiated completely. The vertical jaw 330 moves to a top of the second non-zero fluence region B and the second group of leaf pairs 315 are completely exposed from the vertical jaw 330. FIG. 5(g) shows final positions of the leaf pairs 315, 316 when the fluence map has completely radiated. From the step 701 to the step 704, the leaf pairs 316 in the third group are not shaded by the vertical jaw 330.

In FIGS. 5(a)-5(g), the vertical dimension of the first non-zero fluence region A is same to that of second non-zero fluence region B. The number of the leaf pairs 313 in the first group is identical to that of the leaf pairs 315 in the second group. Optionally, the vertical dimension of the first non-zero fluence region A can be different from that of second non-zero fluence region B. When the vertical dimension of the first non-zero fluence region A is greater than that of second non-zero fluence region B, the number of the leaf pairs 313 in the first group is more than that of the leaf pairs 315 in the second group. When the vertical dimension of the first non-zero fluence region A is smaller than that of second non-zero fluence region B, the number of the leaf pairs 313 in the first group is less than that of the leaf pairs 315 in the second group. The above relationship between the leaf pairs 313 and 315 can be applied not only in the first embodiment, but also can be applied in the following second embodiment and the third embodiment.

Figure 7:
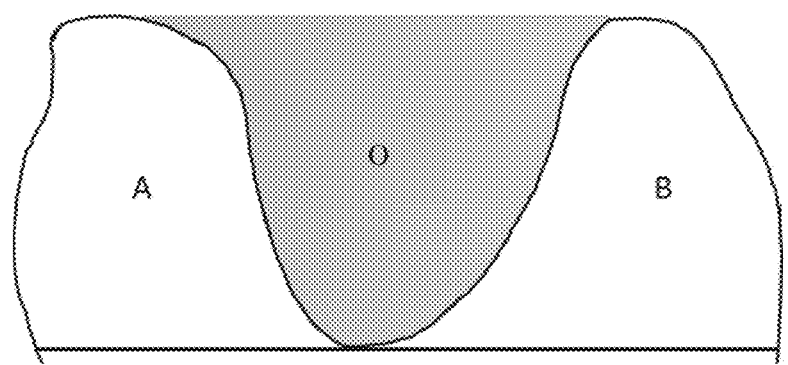
FIG. 7 is a schematic figure of the substantially U-shaped fluence map referred in a second embodiment comprising a first and second non-zero fluence regions.
Figure 8:
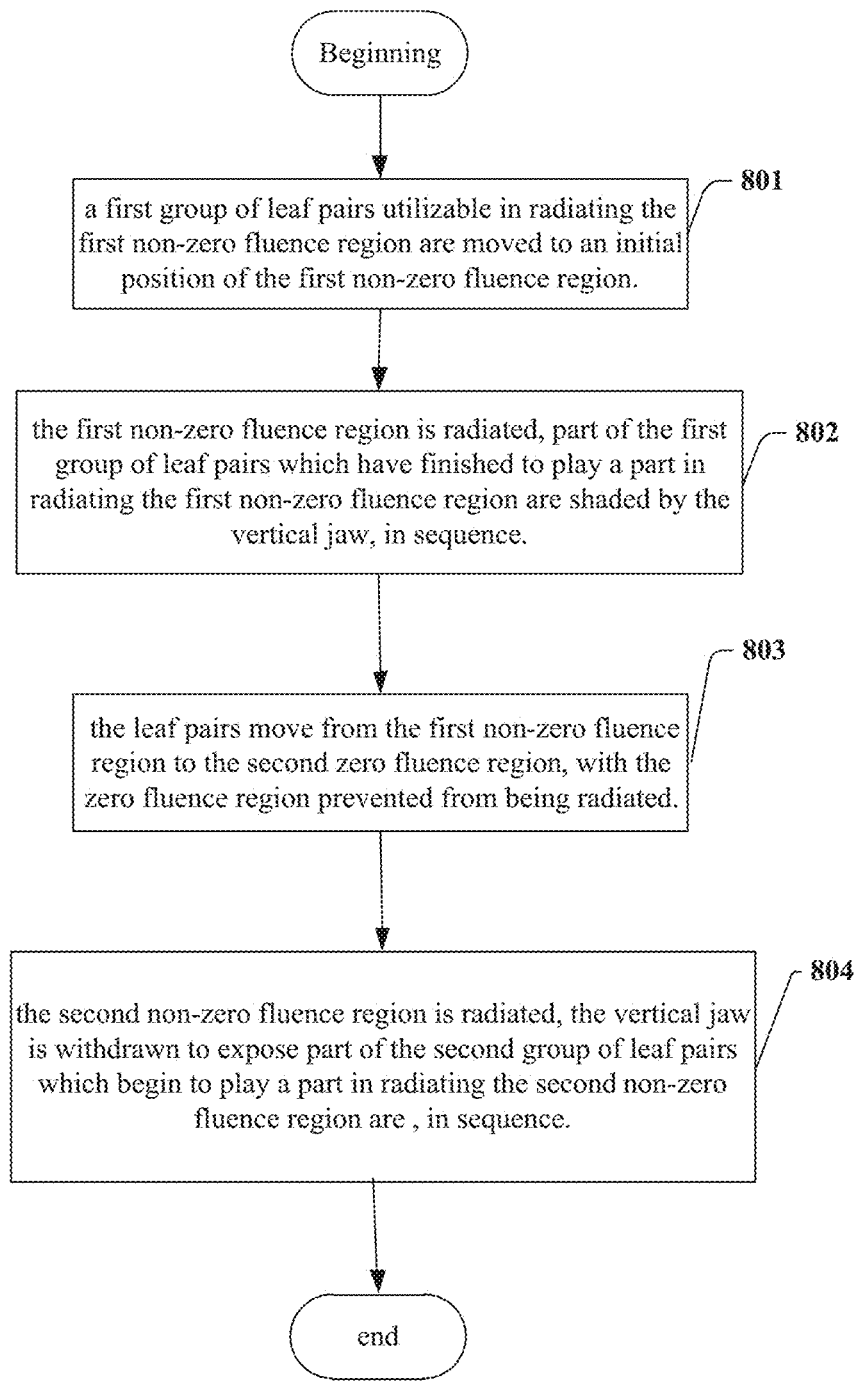
FIG. 8 is a flowchart showing a process of radiating the fluence map referred in the second embodiment of the present invention.

FIG. 8 is a flowchart showing a process of radiating another substantially U-shaped fluence map having a zero fluence region referred in a second embodiment. The fluence map in the second embodiment, as shown in FIG. 7, comprises a first non-zero fluence region A and a second non-zero fluence region B, lack of a third non-zero fluence region.

In a step 801, a first group of leaf pairs in the second embodiment utilizable in radiating the first non-zero fluence region A are moved to an initial position of the first non-zero fluence region A.

In the step 802, the first non-zero fluence region is radiated from left to right gradually through the opening between the leaves of the leaf pairs in the first group, along with the movement of the leaf pairs in the first group and the downwardly movement of the vertical jaw 330. In the process of radiating the first non-zero fluence region A, part of the leaf pairs 313 which have already finished to play a part in radiating the first non-zero fluence region A are shaded by the vertical jaw 330 under the downwardly movement of the vertical jaw 330, in sequence.

In the step 803, the MLC 310 continues to move along the direction from left to right, to carry a second group of the leaf pairs of the MLC to an initial position of the second non-zero fluence region B. The zero fluence region is prevented from being radiated when the leaf pairs move from the first non-zero fluence region A to the second non-zero fluence region B, since the zero fluence region is shaded by the vertical jaw when the vertical jaw 330 arrives at the bottom of the first non-zero fluence region A, i.e., at a bottom of the zero fluence region.

In the step 804, the vertical jaw is withdrawn upwardly to expose the leaf pairs which begin to play a part in radiating the second non-zero fluence region B in sequence, when the second non-zero fluence region B is radiated. Once the MLC 310 arrives at the bottom of the first non-zero fluence region A, the MLC 310 begins to leave from the bottom. The end of step 802 and the beginning of the step 804 happen almost the same time, with the MLC 310 and the vertical jaw 330 moving constantly.

A fluence map (not shown) in a third embodiment is similar to that in the first embodiment, except that the zero fluence region between the first non-zero fluence region and the second non-zero fluence region in the third embodiment has a substantially flat bottom edge to make a middle part of the third non-zero fluence region below the flat bottom edge not aligned with the first non-zero fluence region or the second non-zero fluence region. An additional step 903 of radiating the middle part of the third non-zero fluence region C with the vertical jaw 330 remaining static is added.

Figure 9:
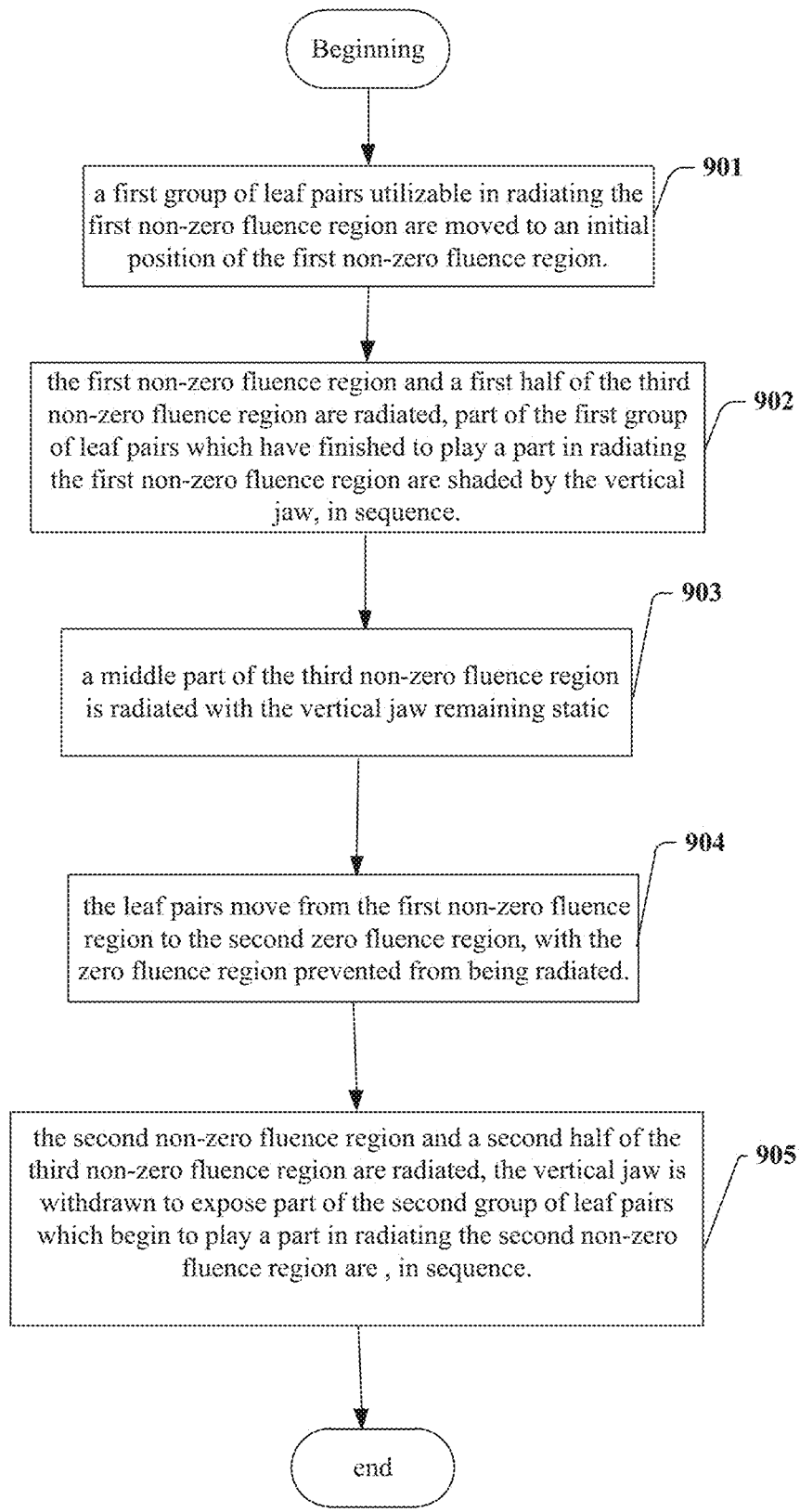
FIG. 9 is a flowchart showing a process of radiating the fluence map referred in a third embodiment of the present invention.

FIG. 9 is a flowchart showing a process of radiating the substantially U-shaped fluence map having the zero fluence region referred in the third embodiment. In the step 901, a first group of leaf pairs utilizable in radiating the first non-zero fluence region A are moved to an initial position of the first non-zero fluence region A. A third group of leaf pairs utilizable in radiating a left half of the third non-zero fluence region C are moved to a left edge of the third non-zero fluence region C.

In the step 902, the first non-zero fluence region A and the left half of the third non-zero fluence region C are radiated from left to right gradually, along with the movement of the leaf pairs. In the process of radiating the first non-zero fluence region A and the left half of third non-zero fluence region C, part of the leaf pairs 313 which have already finished to play a part in radiating the first non-zero fluence region A are shaded by the vertical jaw 330 under the downwardly movement of the vertical jaw 330, in sequence.

When the vertical jaw 330 arrives at a bottom of the first non-zero fluence region A, the step 903 is taken. In the step 903, only the middle part of the third non-zero fluence region C is radiated, with the leaf pairs moving rightward and the vertical jaw 330 remaining static.

In the step 904, the MLC 310 continues to move along the direction from left to right, to carry the second group of the leaf pairs 315 to an initial position of the second non-zero fluence region B. The zero fluence region is prevented from being radiated when the leaf pairs move from the first non-zero fluence region A to the second non-zero fluence region B, since the zero fluence region is shaded by the vertical jaw 330 when the vertical jaw 330 arrives at the bottom of the first non-zero fluence region A, i.e., at a bottom of the zero fluence region.

In the step 905, the vertical jaw 330 is withdrawn upwardly to expose the leaf pairs which begin to play a part in radiating the second non-zero fluence region B in sequence, when the second non-zero fluence region B and right half of the third non-zero fluence region C are radiated.

In a fourth embodiment, the fluence map is formed in a substantially X-shape has two zero-fluence regions. A process of radiating a substantially X-shaped fluence map shown in FIG. 2(c) is illustrated below. Two vertical jaws 330 are used in shading the upper leaves and lower leaves of MLC 310.

Figure 10:
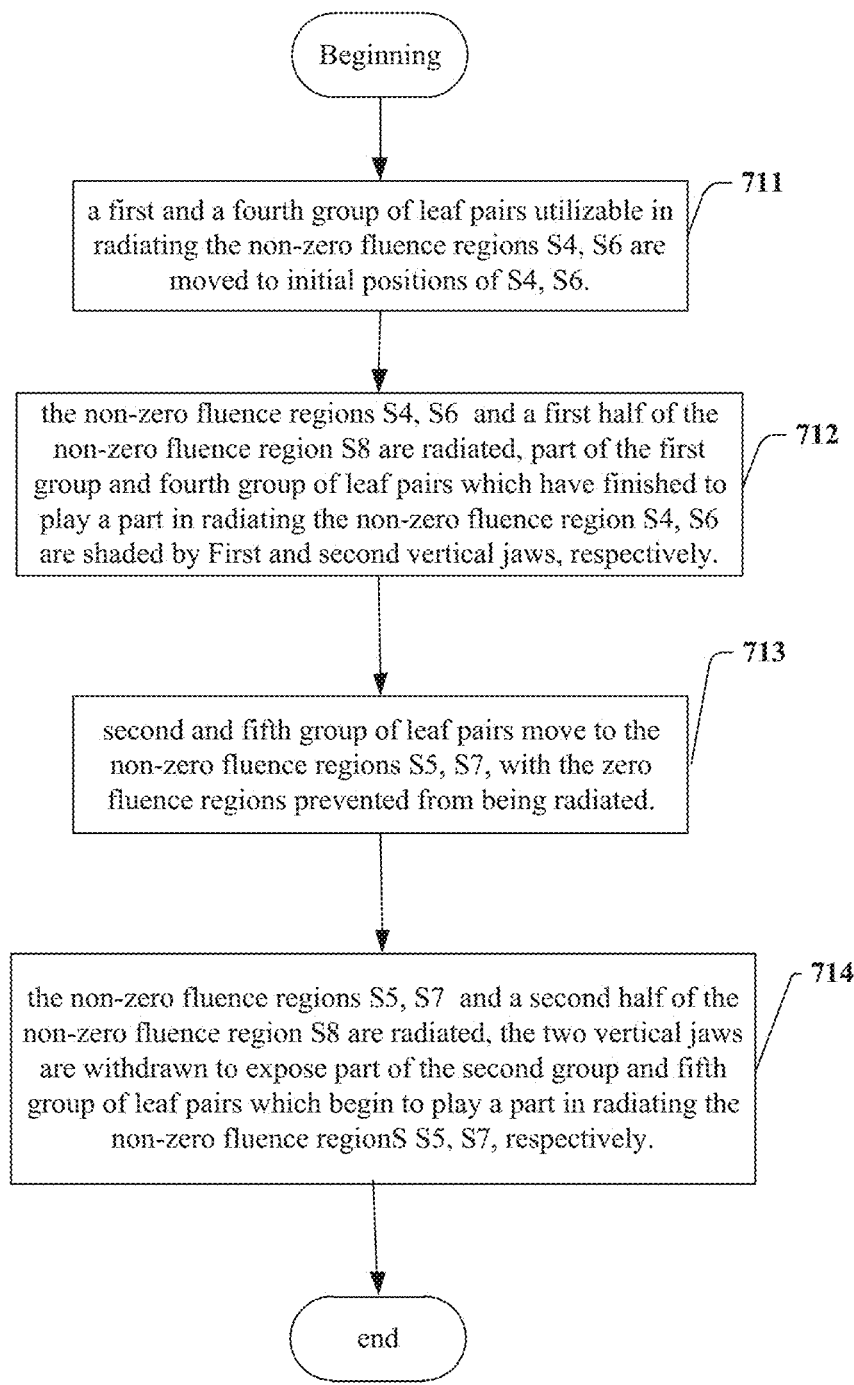
FIG. 10 is a flowchart showing a process of radiating a substantially X-shaped fluence map having two zero-fluence regions referred in a fourth embodiment of the present invention.

FIG. 10 is a flowchart showing a process of radiating the substantially X-shaped fluence map, as shown in FIG. 2(c), having two zero fluence regions referred in the fourth embodiment). In a step 711, a first group of leaf pairs utilizable in radiating the non-zero fluence region S4 are moved to an initial position of the non-zero fluence region S4, and a fourth group of leaf pairs utilizable in radiating the non-zero fluence region S6 are moved to an initial position of the non-zero fluence region S6. A third group of leaf pairs utilizable in radiating a left half of the non-zero fluence region S8 are moved to a left edge of the non-zero fluence region S8.

In the step 712, the non-zero fluence region S4 is radiated from left to right gradually through the opening between the leaves of the leaf pairs 313 in the first group, along with the movement of the first group of leaf pairs and the downwardly movement of the first vertical jaw. Meanwhile, the non-zero fluence region S6 is radiated from left to right gradually through the opening between the leaves of the leaf pairs in the fourth group, along with the movement of the fourth group of leaf pairs and the upwardly movement of the second vertical jaw. In the above process, the left half of the non-zero fluence region S8 is radiated from left to right gradually. In the process of radiating the non-zero fluence region S4 and the non-zero fluence region S6, part of the leaf pairs which have already finished to play a part in radiating the non-zero fluence region S4 are shaded by the first vertical jaw under the downwardly movement of the first vertical jaw, and part of the leaf pairs which have already finished to play a part in radiating the non-zero fluence region S6 are shaded by the second vertical jaw under the upwardly movement of the second vertical jaw, in sequence.

In the step 713, a second group of the leaf pairs are moved to an initial position of the non-zero fluence region S5 and a fifth group of the leaf pairs are moved to an initial position of the non-zero fluence region S7. The zero fluence regions are shaded by the first and second jaws and thereby prevented from being radiated.

In the step 714, the first vertical jaw is withdrawn upwardly to expose part of the second group of leaf pairs which begin to play a part in radiating the non-zero fluence region S5, the second vertical jaw is withdrawn downwardly to expose part of the fifth group of leaf pairs which begin to play a part in radiating the non-zero fluence region S7.

If there is only one zero-fluence region in the fluence map, the fluence map can be formed into a U shape opened upwardly as shown in FIG. 2(b) or downwardly, or a C shape opened rightward or leftward, or a closed O shape. The leaves of MLC 310 move repeatedly along a left-to-right direction, perpendicular to a top-to-bottom direction. If there are multiple zero-fluence regions in the fluence map, the shape of the fluence map becomes complicated. The C-shaped fluence map, or O-shaped fluence map, or the complicated fluence map having multiple zero-fluence regions in a fifth embodiment can be divided into multiple basic fluence maps. Examples of dividing the C-shaped fluence map, O-shaped fluence map, and the complicated fluence map are respectively illustrated below.

Figure 11A:
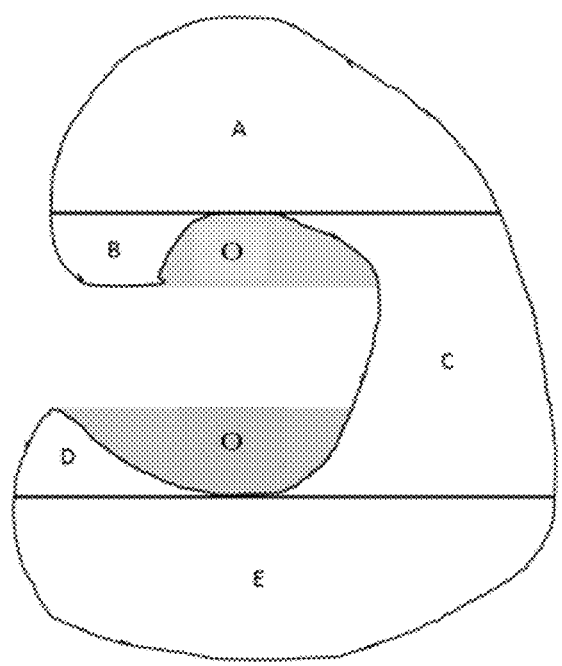
FIGS. 11(a)-11(c) are schematic figures showing a C-shaped fluence map divided into several basic fluence maps in a fourth embodiment.
Figure 11B:
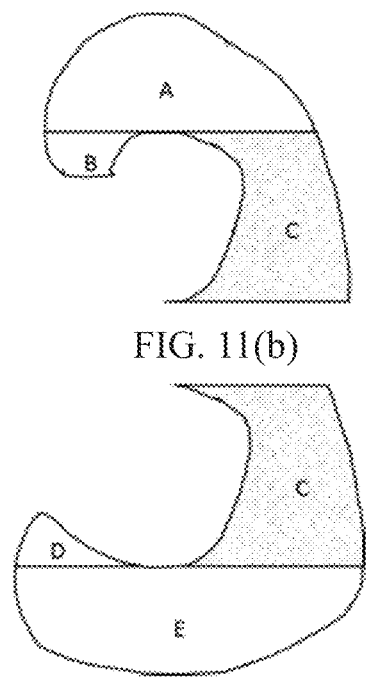
Figure 11C:
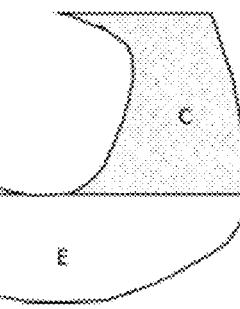

FIGS. 11(a)-11(c) show a C-shaped fluence map divided into several basic fluence maps. The C-shaped fluence map shown in FIG. 11(a), for example, can be divided into two substantially U-shaped basic fluence maps respectively shown in FIGS. 11(b) and 11(c). The substantially U-shaped fluence map shown in FIG. 11(b) contains all the fluence distributed in region A, region B, and half of the fluence distributed in region C. The substantially U-shaped fluence map shown in FIG. 11(c) contains all the fluence distributed in region D, region E, and half of the fluence distributed in region C.

Figure 12A:
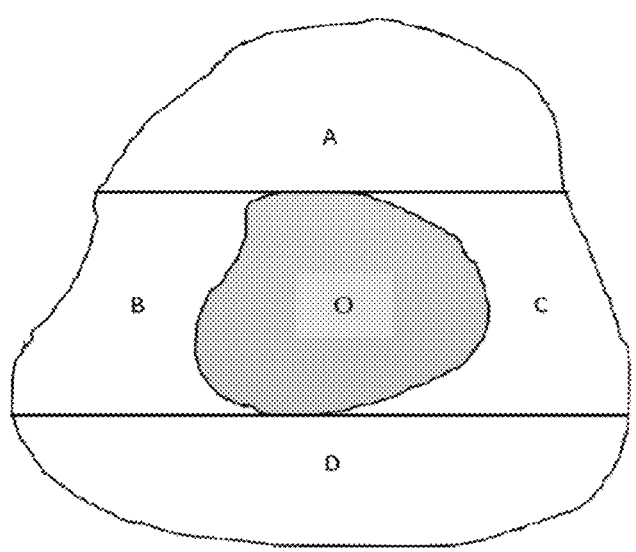
FIGS. 12(a)-12(c) are schematic figures showing an O-shaped fluence map divided into several basic fluence maps in a fifth embodiment.
Figure 12B:
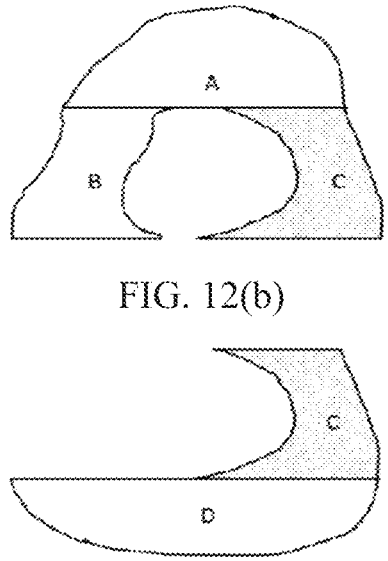
Figure 12C:
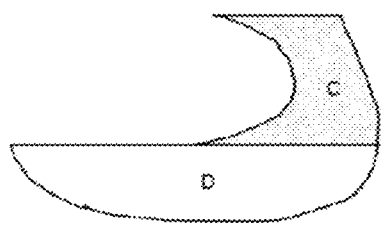

FIGS. 12(a)-12(c) show an O-shaped fluence map divided into several basic fluence maps. The O-shaped fluence map shown in FIG. 12(a), for example, can be divided into two substantially U-shaped fluence maps respectively shown in FIGS. 12(b) and 12(c). The substantially U-shaped fluence map shown in FIG. 12(b) contains all the fluence distributed in region A, region B, and half of the fluence distributed in region C. The substantially U-shaped fluence map shown in FIG. 12(c) contains all the fluence distributed in region D, and half of the fluence distributed in region C.

Figure 13A:
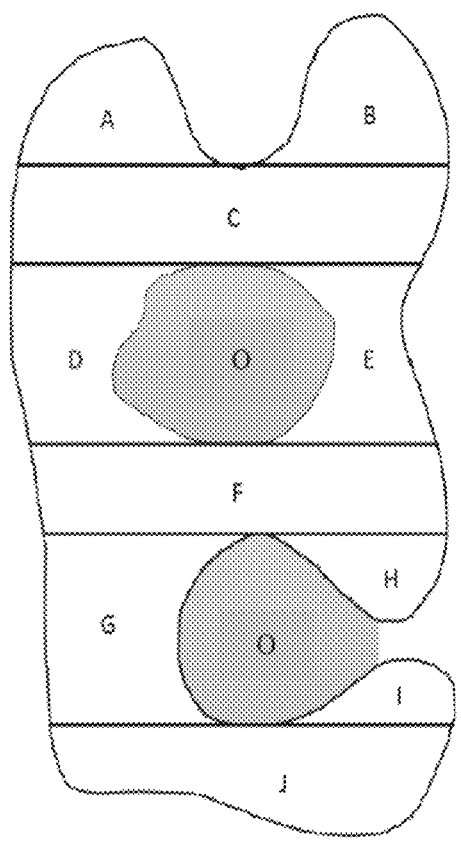
FIGS. 13(a)-13(d) are schematic figures showing a fluence map having a complicated shape divided into several basic fluence maps in the fifth embodiment.
Figure 13B:
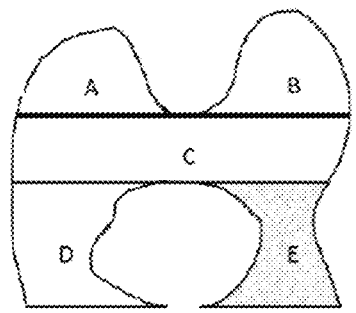
Figure 13C:
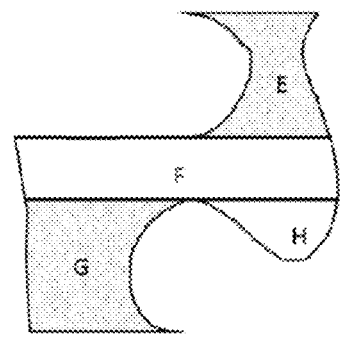
Figure 13D:
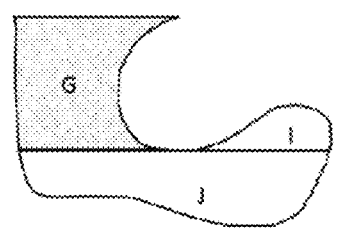

FIG. 13(a) shows a fluence map having a complicated shape and divided into several basic fluence maps shown in FIGS. 13(b)-13(d). The fluence map shown in FIG. 13(a) comprises a U-shaped region, an O-shaped region and a C-shaped region, and for example can be divided into three basic fluence maps, i.e., one substantially X-shaped basic fluence map and two substantially U-shaped basic fluence maps. The substantially X-shaped fluence map shown in FIG. 13(b) contains all the fluence distributed in region A, region B, region C, region D, and half of the fluence distributed in region E. The substantially U-shaped basic fluence map shown in FIG. 13(c) contains half of the fluence distributed in region E, half of the fluence distributed in region G, all the fluence distributed in region F and region H. The substantially U-shaped fluence map shown in FIG. 13(d) contains half of the fluence distributed in region G, all the fluence distributed in region I and region J.

The several basic fluence maps are connected in series. The moving directions of the leaf pairs of one MLC 310 or two MLCs 310 are invariable in radiating a same basic fluence map and need to be converted in different basic fluence maps, which are divided from the O-shaped fluence map, or the C-shaped fluence map, or the fluence map having complicated shape. An initial moving direction of the leaf pairs needs to be determined firstly. For example, when the fluence map shown in FIG. 11(a) is radiated, the leaf pairs move from left to right invariably in radiating the basic fluence map shown in FIG. 11(b), and then move from right to left invariably in radiating the next basic fluence map shown in FIG. 11(c). When the fluence map shown in FIG. 12(a) is radiated, the leaf pairs move from left to right invariably in radiating the basic fluence map shown in FIG. 12(b), and then move from right to left invariably in radiating the next basic fluence map shown in FIG. 12(c). When the fluence map shown in FIG. 13(a) is radiated, the leaf pairs move from left to right invariably in radiating the initial basic fluence map shown in FIG. 13(b), then move from right to left invariably in radiating the next basic fluence map shown in FIG. 13(c), and finally move from left to right invariably in radiating the final basic fluence map shown in FIG. 13(d).

Figure 14:
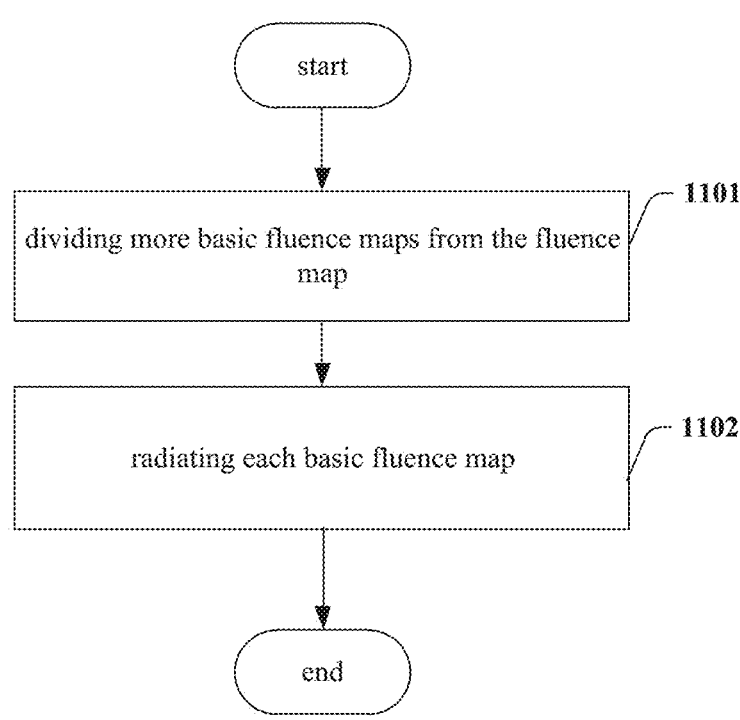
FIG. 14 is a flowchart of primary steps of the radiation method referred in the fifth embodiments.
Figures 15A, 15B, 15C, 15D, 15E, 15F:
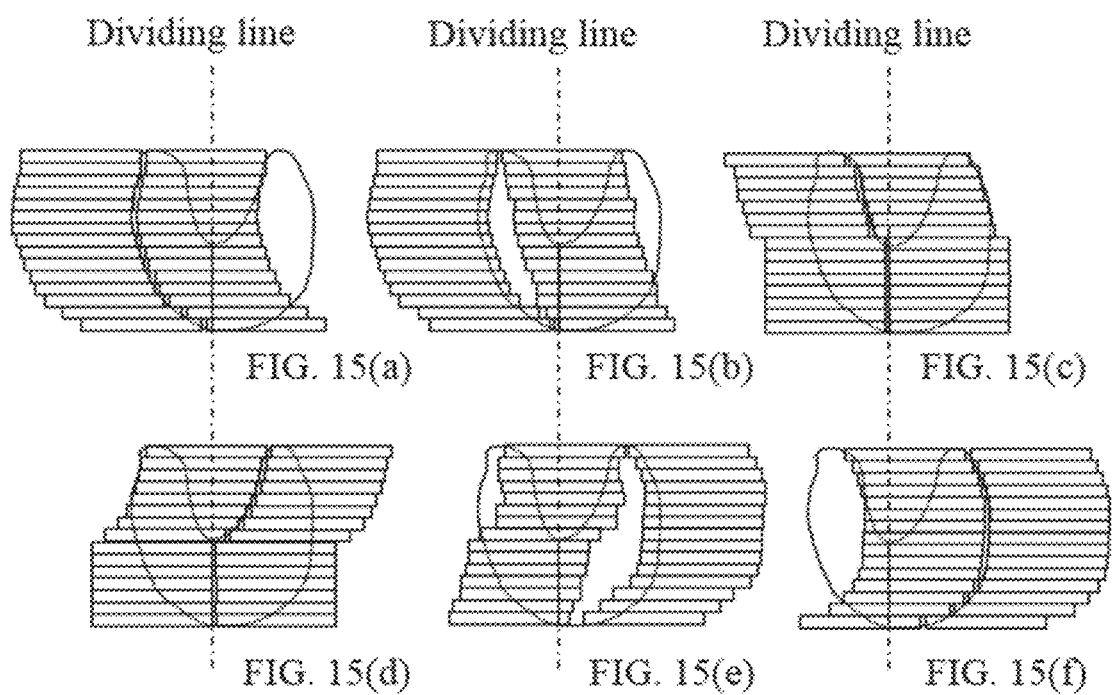
FIGS. 15(a)-15(f) are schematic figures showing a process of the conventional field-dividing method.

FIG. 14 is a flowchart showing a process of radiation method of the fifth embodiments of the present invention.

In the step 1101, a plurality of basic fluence maps are divided from the fluence map having at least one zero-fluence region. The basic fluence map is referred to the convex-shaped basic fluence map shown in FIG. 2(a), or the substantially U-shaped fluence map referred in the first through the third embodiment, or the substantially X-shaped fluence map referred in the fourth embodiment shown in FIG. 2(c). The basic fluence map can be radiated once along an invariable direction. In the step 1102, each basic fluence map is radiated.

Specifically, when the basic fluence map is convex-shaped shown in FIG. 2(a), the convex-shaped basic fluence map is radiated once when the MLC 310 is moved along the invariable direction, without the participation of the vertical jaw. The step 1102 includes the step of radiating the basic fluence map directly under the movement of the MLC 310.

When the basic fluence map is substantially U-shaped, the substantially U-shaped basic fluence map in the first through third embodiment is radiated once when the MLC 310 is moved along the invariable direction, along with the movement of the vertical jaw 330. Referring to FIGS. 6 and 5(a), the first group of leaf pairs 313 utilizable in radiating the first non-zero fluence region A are moved to an initial position Pa of the first non-zero fluence region A.

The first non-zero fluence region A is radiated from left to right gradually through an upper part of the opening between the leaves of the leaf pairs 313 in the first group, along with the movement of the leaf pairs 313 and the downwardly movement of the vertical jaw 330. In the process of radiating the first non-zero fluence region A, part of the leaf pairs 313 which have already finished to play a part in radiating the first non-zero fluence region A are shaded by the vertical jaw 330 under the downwardly movement of the vertical jaw 330, in sequence.

Referring to FIG. 5(b), the leaf pairs 313, 316 move along a direction from left to right gradually. The first non-zero fluence region A is radiated through the opening between the leaves in the leaf pairs 313. Referring to FIG. 5(c), the uppermost leaf pair 313a, which has already finished to play a part in radiating the uppermost part of the first non-zero fluence region A, is partially shaded by the vertical jaw 330, along with the downwardly movement of the vertical jaw 330. Referring to FIG. 5(d), the upper leaf pairs of the leaf pairs 313, which have finished to play a part in radiating the upper portion of first non-zero fluence region A, are shaded by the perpendicular jaw 330, along with the further downwardly movement of the vertical jaw 330. The first non-zero fluence region A continue to be radiated through the opening between the leaves of the unshaded leaf pairs of the leaf pairs 313 in the first group. Referring to FIG. 5(e), the vertical jaw 330 continues to move downwardly till arriving at a bottom of the first non-zero fluence region A. The first non-zero fluence region A is completely shaded by the vertical jaw 330 at that moment. The first non-zero fluence region A is radiated completely.

MLC continues to move along the direction from left to right, to carry the leaf pairs 315 in the second group to an initial position Pb of the second non-zero fluence region B. The zero fluence region is prevented from being radiated when the leaf pairs 315 move from the first non-zero fluence region A to the second zero fluence region B, since the zero fluence region is shaded by the vertical jaw 330 when the vertical jaw 330 arrives at the bottom of the first non-zero fluence region A, i.e., at a bottom of the zero fluence region.

The vertical jaw 330 is withdrawn upwardly from the leaf pairs 315 gradually in radiating the second non-zero fluence region B.

Referring to FIGS. 5(e) and 5(f), the second non-zero fluence region B begins to be radiated and then is radiated gradually through the opening between the leaves in the leaf pairs 315 in the second group, along with the movement of the leaf pairs 315 and the upwardly movement of the vertical jaw 330. In the process of radiating the second non-zero fluence region B, the vertical jaw 330 is withdrawn to expose part of the leaf pairs 315 which begin to play a part in radiating the second non-zero fluence region B, gradually.

Referring to FIG. 5(f), the second non-zero fluence region B continues to be radiated through the opening between the leaves of the rest leaf pairs 315 in the second group. Referring to FIG. 5(g), the vertical jaw 330 moves to a top of the second non-zero fluence region B and the second non-zero fluence region B is completely exposed from the vertical jaw 330. FIG. 5(g) shows final positions of the leaf pairs 315 when the basic fluence map has been completely radiated.

The first and second non-zero fluence regions A, B are radiated only, or radiated together with the third non-zero fluence region C in the above process.

When the basic fluence map is substantially X-shaped, the steps 711-714 are included.

The MLC 310 is moved repeatedly along the right-to-left direction in radiating different basic fluence maps.

As to a radiation method of radiating the fluence map, firstly, whether there is any zero-fluence region existed in the fluence map should be considered. If there is no zero-fluence region existed in the fluence map, the fluence map can be radiated directly under the movement of the MLC 310.

If there is a zero-fluence region existed in the fluence map, determining one basic fluence map, i.e., the fluence map itself, or dividing a plurality of basic fluence maps connected in series from the fluence map as introduced in the step 1101, on consideration of the position of the zero-fluence region.

A radiating step is taken then. When only one basic fluence map is determined, radiating the basic fluence map. When a plurality of basic fluence maps connected in series are divided from the fluence map, the plurality of basic fluence maps are radiated in sequence, under the cooperation of the MLC 310 and the vertical jaw 330. As to the fluence map in the fifth embodiment, the fluence map should be divided into several basic fluence maps in the dividing step 1101, and then the basic fluence maps are radiated one by one in the radiating step 1102.

The fluence map having U-shape, or X-shape, or C-shape, or O-shape, or other complicated shapes can be radiated once, rather than several times. It doesn't need to close the radiation in the whole radiating process. MU in the present invention is correspondingly reduced. In addition, it will be more efficiently to radiate the fluence map of the present invention, since the "set-up time" is saved. The treatment time may be reduced accordingly. Furthermore, the fluence map is radiated once, therefore dose delivered at the edge of adjacent fluence region is accurate.

As to the fluence map having more than one C-shaped fluence region or O-shaped fluence region, it will be more efficiently to use the conventional field-dividing method than the radiation method of the present invention, so it will be better to use the conventional field-dividing method to radiate the fluence map having more than one C-shaped fluence region or O-shaped fluence region.

Although radiation is conducted by the prior jaws and MLC in the above embodiment, it can be understood by the one of skilled in the art that, the jaws herein can be replaced by other movable blocks substantially not transparent to X-rays.

The radiation method and apparatus used in radiating the fluence map in the above embodiments of the present invention can be implemented by computer readable medium, such as software, hardware, or combination of software and hardware of computer. As for the implementation by hardware, the embodiment recited by the present invention can be implemented by one or more ASIC (Application Specific Integrated Circuit), DSP (Digital Signal Processing), DAPD (Distributed and Parallel Database), PLD (Programmable Logic Device), FPGA (Field Programmable Gate Array), processors, controllers, microcontrollers, microprocessors, other electronic components for implementing the above-mentioned function, or optional combinations of the above components. Under some circumstances, the embodiment can be implemented by controllers.

As to the implementation by software, the embodiment recited by the present invention can be implemented by independent modules, such as procedure module and/or function module. Each independent module can implement one or more functions or operations recited before. The software code can be implemented in an application programmed by proper programing language, and can be stored in a memory, and implemented by controller or processor. For example, according to the present invention, a radiation apparatus used in radiating a fluence map having a zero fluence region distributed along a moving direction of the leaf pairs of MLC, or along a direction parallel to the moving direction of the leaf pairs of MLC.

The apparatus comprises a determining module and a driving module. The determining module is used to determine one or more basic fluence maps from the fluence map. The basic fluence map can be radiated once along an invariable direction. The basic fluence map of a first style of shape can be radiated under the movement of the MLC 310 directly, such as a convex-shaped basic fluence map. The basic fluence map of a second style of shape can be divided into zero fluence region and non-zero fluence regions, and can be radiated by the cooperation MLC and one vertical jaw, such as the U-shaped basic fluence map, or can be radiated by the cooperation of MLC and two or more vertical jaws, such as X-shaped basic fluence map. The driving module is used in radiating the basic fluence map of the second style of shape. The driving module is used to move the leaf pairs 313 of the first group to the initial position Pa of the first non-zero fluence region A, drive the leaf pairs 313, 316 move in the first non-zero fluence region A and the third non-zero fluence region C, move the vertical jaw 300 along a direction perpendicular to the moving direction of the leaf pairs 313 to shade the leaf pairs 313, drive the leaf pairs 315, 316 move in the second non-zero fluence region A and the third non-zero fluence region C, and withdraw the vertical jaw 330 from shading the leaf pairs 315 in radiating the second non-zero fluence region B.

Although the present invention is described in accordance with the current specific embodiments, it is to be understood by one of skilled in the art that the above embodiments are illustrative of the principles of the present invention. Other equivalent modifications or substitutions may also be employed without departing from the spirit of the present invention. Thus, various variations or modifications within the above embodiment within the spirit of the present invention may be within the scope of the claims of the present application.

I claim:

1. A method for radiating a target fluence map under a movement of a plurality of leaf pairs of a multi-leaf collimator (MLC), comprising:
   determining whether the target fluence map is a basic fluence map, wherein the basic fluence map is capable of being radiated in a single radiation delivery; and
   in response to determining that the target fluence map is not a basic fluence map,
      generating two or more basic fluence maps connected in series based on the target fluence map; and
      performing radiation of the two or more basic fluence maps in sequence, wherein each of the two or more basic fluence maps that is different is radiated differently.

2. The method of claim 1, wherein at least one of the two or more basic fluence maps includes a zero fluence region located between two non-zero fluence regions in a movement direction of the plurality of leaf pairs, and each one of the two or more basic fluence maps partially overlaps one or more other basic fluence maps of the two or more basic fluence maps.

3. The method of claim 1, wherein the MLC further includes one or more jaws, and the performing radiation of the two or more basic fluence maps in sequence comprises:
   performing radiation of the at least one basic fluence map, including:
      radiating a first portion of the at least one basic fluence map by moving a first group of leaf pairs of the plurality of leaf pairs in a first direction and moving a first jaw in a second direction to shade the first group of leaf pairs in sequence.

4. The method of claim 3, wherein the performing radiation of the at least one basic fluence map further including:
   radiating a second portion of the at least one basic fluence map by moving a second group of leaf pairs of the plurality of leaf pairs in the first direction and moving the first jaw in a third direction to expose the second group of leaf pairs in sequence.

5. The method of claim 4, wherein the second direction is perpendicular to the first direction, the third direction is opposite to the second direction, and at least one leaf pair belongs to both the first group of leaf pairs and the second group of leaf pairs.

6. The method of claim 4, wherein performing radiation of the at least one basic fluence map further including:
   radiating a third portion of the at least one basic fluence map by moving a third group of leaf pairs of the plurality of leaf pairs in a fourth direction and moving a second jaw in a fifth direction to shade the third group of leaf pairs in sequence.

7. The method of claim 6, wherein performing radiation of the at least one basic fluence map further including:
   radiating a fourth portion of the at least one basic fluence map by moving a fourth group of leaf pairs of the plurality of leaf pairs in the fourth direction and moving the second jaw in a sixth direction to expose the fourth group of leaf pairs in sequence.

8. The method of claim 7, wherein
   the fourth direction is the same as the first direction,
   the fifth direction is opposite to the second direction, and
   the sixth direction is opposite to the third direction.

9. The method of claim 7, wherein
   at least a portion of the first portion of the at least one basic fluence map and at least a portion of the third portion of the at least one basic fluence map are radiated simultaneously; or at least a portion of the second portion of the at least one basic fluence map and at least a portion of the fourth portion of the at least one basic fluence map are radiated simultaneously.

10. The method of claim 1, wherein the two or more basic fluence maps include a first basic fluence map and a second basic fluence map, the first basic fluence map and the second basic fluence map including an overlapping region, the overlapping region having a target fluence, and the method further comprises:
radiating the overlapping region with half of the target fluence while radiating the first basic fluence map; and
radiating the overlapping region with half of the target fluence while radiating the second basic fluence map.

11. A method for radiating a target fluence map under a movement of a plurality of leaf pairs of a multi-leaf collimator (MLC), comprising:
determining whether the target fluence map includes a zero fluence region;
in response to determining that the target fluence map includes a zero fluence region,
performing radiation of the target fluence map by moving at least one portion of the plurality of leaf pairs and moving a jaw based on a movement status of the at least one portion of the plurality of leaf pairs.

12. The method of claim 11, wherein
the jaw is configured to prevent radiation of the zero fluence region during the movement of the at least one portion of the plurality of leaf pairs.

13. The method of claim 11, wherein the performing radiation of the target fluence map by moving at least one portion of the plurality of leaf pairs, and moving a jaw based on a movement status of the at least one portion of the plurality of leaf pairs comprises:
radiating a first portion of the target fluence map by moving a first group of leaf pairs of the plurality of leaf pairs in a first direction and moving the jaw in a second direction to shade the first group of leaf pairs in sequence; and
radiating a second portion of the target fluence map by moving a second group of leaf pairs of the plurality of leaf pairs in the first direction and moving the jaw in a third direction to expose the second group of leaf pairs in sequence.

14. A method for radiating a complex fluence map under a movement of a plurality of leaf pairs of a multi-leaf collimator (MLC), comprising:
divide, based on a shape of the complex fluence map, the complex fluence map with at least one zero-fluence region into one or more basic fluence maps, wherein the basic fluence map is capable of being radiated in a single radiation delivery, and the basic fluence map includes a convex-shaped basic fluence map, a U-shaped basic fluence map, or an X-shaped basic fluence map; and
performing radiation on the one or more basic fluence maps in sequence under a cooperation of the MLC and a vertical jaw based on shapes of the one or more basic fluence maps.

15. The method of claim 14, wherein performing radiation on the one or more basic fluence maps when the one or more basic fluence maps include the convex-shaped basic fluence map comprises:
performing radiation on the convex-shaped basic fluence map under a movement of the MLC being moved along an invariable direction without a movement of the vertical jaw.

16. The method of claim 14, wherein performing radiation on the one or more basic fluence maps when the one or more basic fluence maps include the U-shaped basic fluence map comprises:
performing radiation on the convex-shaped basic fluence map under a movement of the MLC being moved along an invariable direction and a movement of the vertical jaw.

17. The method of claim 14, wherein performing radiation on the one or more basic fluence maps when the one or more basic fluence maps include the X-shaped basic fluence map comprises:
performing radiation on the convex-shaped basic fluence map under a movement of the MLC being moved along an invariable direction and a movement of two vertical jaws.

18. The method of claim 14, wherein the complex fluence map is divided into two substantially U-shaped basic fluence maps when the complex fluence map is a C-shaped map.

19. The method of claim 14, wherein the complex fluence map is divided into two substantially U-shaped basic fluence maps when the complex fluence map is an O-shaped map.

20. The method of claim 14, wherein the complex fluence map is divided into at least one U-shaped basic fluence maps and at least one X-shaped basic fluence maps when the complex fluence map is composed of an O-shape, a U-shape, and a C-shape.

* * * * *